United States Patent
Dayton et al.

(10) Patent No.: US 10,912,566 B2
(45) Date of Patent: Feb. 9, 2021

(54) SYSTEMS AND METHODS TO EFFECT MOVEMENT OF TISSUE STRUCTURES

(71) Applicant: Boston Scientific Scimed, Inc., Maple Grove, MN (US)

(72) Inventors: Peter L. Dayton, Brookline, MA (US); Katharine Eckerline, Boston, MA (US); Douglas Melanson, Natick, MA (US); Raymond Gessler, Roberts, WI (US); Barry Weitzner, Acton, MA (US); Jeff Gray, Sudbury, MA (US); Nicholas Zenner, White Bear Township, MN (US); Ryan Hartman, Duxbury, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 277 days.

(21) Appl. No.: 15/935,969

(22) Filed: Mar. 26, 2018

(65) Prior Publication Data
US 2018/0271530 A1    Sep. 27, 2018

Related U.S. Application Data

(60) Provisional application No. 62/476,995, filed on Mar. 27, 2017.

(51) Int. Cl.
  *A61B 17/11* (2006.01)
  *A61B 1/018* (2006.01)
  (Continued)

(52) U.S. Cl.
  CPC .............. *A61B 17/11* (2013.01); *A61B 1/018* (2013.01); *A61B 8/12* (2013.01); *A61B 17/1114* (2013.01);
  (Continued)

(58) Field of Classification Search
  CPC .......... A61B 2017/1139; A61B 17/114; A61B 2017/1103; A61B 2017/22044;
  (Continued)

(56) References Cited

U.S. PATENT DOCUMENTS

| 6,092,526 A * | 7/2000 | LaFontaine | A61B 17/11 128/898 |
| 7,988,690 B2 | 8/2011 | Chanduszko et al. | |

(Continued)

FOREIGN PATENT DOCUMENTS

| EP | 1901661 A2 | 3/2008 |
| EP | 2760371 A1 | 8/2014 |

(Continued)

OTHER PUBLICATIONS

"Stone Cone," http://www.bostonscientific.com/en-US/products/antiretropulsion/stone-cone.html (Dec. 2016).

(Continued)

*Primary Examiner* — Christine H Matthews
*Assistant Examiner* — Joshua Daryl D Lannu
(74) *Attorney, Agent, or Firm* — Kacvinsky Daisak Bluni PLLC (57) ABSTRACT

The present disclosure relates generally to medical devices and procedures for placement of a medical device between adjacent tissue structures. In particular, the present disclosure relates to endoscopic systems and methods for preventing or minimizing movement between tissue walls to facilitate placement of a stent therebetween.

20 Claims, 10 Drawing Sheets

(51) Int. Cl.
  *A61B 8/12*     (2006.01)
  *A61B 17/34*    (2006.01)
  *A61F 2/95*     (2013.01)
  *A61B 17/00*    (2006.01)
  *A61B 17/22*    (2006.01)
  *A61F 2/04*     (2013.01)
  *A61F 2/90*     (2013.01)
  *A61F 2/06*     (2013.01)
  *A61F 2/966*    (2013.01)

(52) U.S. Cl.
  CPC ...... *A61B 17/3468* (2013.01); *A61B 17/3478* (2013.01); *A61F 2/95* (2013.01); *A61B 2017/0034* (2013.01); *A61B 2017/00278* (2013.01); *A61B 2017/00349* (2013.01); *A61B 2017/00818* (2013.01); *A61B 2017/00862* (2013.01); *A61B 2017/00867* (2013.01); *A61B 2017/00986* (2013.01); *A61B 2017/1103* (2013.01); *A61B 2017/1139* (2013.01); *A61B 2017/22042* (2013.01); *A61B 2017/22044* (2013.01); *A61B 2017/22047* (2013.01); *A61B 2017/3425* (2013.01); *A61B 2017/3435* (2013.01); *A61F 2/064* (2013.01); *A61F 2/90* (2013.01); *A61F 2/966* (2013.01); *A61F 2002/045* (2013.01); *A61F 2230/001* (2013.01)

(58) Field of Classification Search
  CPC ........... A61B 2017/22047; A61B 2017/22042; A61B 17/11; A61B 2017/3425; A61B 2017/3435; A61B 2017/00818; A61B 8/12; A61B 2017/00278; A61B 2017/00986; A61B 17/3478; A61B 1/018; A61B 2017/00349; A61B 2017/0034; A61B 2017/00862; A61B 2017/00867; A61B 17/3468; A61F 2230/001; A61F 2/064; A61F 2/966; A61F 2/90; A61F 2/95; A61F 2002/045

See application file for complete search history.

(56) References Cited

U.S. PATENT DOCUMENTS

| | | | |
|---|---|---|---|
| 2004/0073237 A1* | 4/2004 | Leinsing | A61B 17/064 606/151 |
| 2004/0122456 A1 | 6/2004 | Saadat | |
| 2005/0251160 A1 | 11/2005 | Saadat | |
| 2010/0268029 A1 | 10/2010 | Phan et al. | |
| 2012/0136426 A1 | 5/2012 | Phan et al. | |
| 2013/0090684 A1* | 4/2013 | Van Bladel | A61B 17/00234 606/213 |
| 2013/0211415 A1 | 8/2013 | Zerfas | |
| 2015/0038988 A1 | 2/2015 | Tegels et al. | |
| 2016/0074626 A1* | 3/2016 | Weadock | A61M 25/0169 600/3 |

FOREIGN PATENT DOCUMENTS

| | | |
|---|---|---|
| JP | 2007519489 A | 7/2007 |
| JP | 2012524616 A | 10/2012 |

OTHER PUBLICATIONS

Itoi et al., "Novel EUS-guided gastrojejunostomy technique using a new double-balloon enteric tube and lumen-apposing metal stent (with videos)," Gastrointestinal Endoscopy, vol. 78, No. 6, pp. 934-939 (2013).

International Search Report and Written Opinion (dated Jun. 15, 2018), for PCT/US2018/024341 (11 pages).

* cited by examiner

SYSTEMS AND METHODS TO EFFECT MOVEMENT OF TISSUE STRUCTURES

CROSS REFERENCE TO RELATED APPLICATIONS

The present application claims the benefit of priority under 35 U.S.C. § 119 to U.S. Provisional Patent Application Ser. No. 62/476,995, filed on Mar. 27, 2017, which is incorporated by reference in its entirety for all purposes.

FIELD

The present disclosure relates generally to the field of devices and procedures for placement of a medical device between adjacent tissue structures. In particular, the present disclosure relates to endoscopic systems and methods for preventing or minimizing movement between tissue walls to facilitate placement of a stent therebetween.

BACKGROUND

Although endoscopic imaging modalities, such as fluoroscopy and endoscopic ultrasound (EUS), allow visualization of anatomical structures beyond the tissue directly in front of the endoscope, the inability to control (e.g., stabilize, immobilize, anchor, etc.) these distal anatomical structures during an endoscopy procedure presents challenges. For example, medical procedures such as gastrojejunostomy, hepaticogastrostomy, and gallbladder drainage, require the placement of a conduit (e.g., stent, etc.) within the appropriate portions of proximal and distal tissue walls. The tendency to lose control of the distal tissue wall during transmural stent deployment procedures presents a significant technical challenge to medical professionals, especially when a direct visual image of the distal tissue wall is unavailable. Failure to properly position the fluid conduit within the appropriate portions of the tissue walls may lead to serious medical complications.

A variety of advantageous medical outcomes may be realized by the systems and/or methods of the present disclosure, which minimize or prevent proximal and distal tissue walls from moving away from each other during a transmural stent placement procedure.

SUMMARY

In one aspect, the present disclosure relates to a system comprising a needle that includes a proximal end, a sharpened distal end, and a lumen extending therebetween. An elongate member may be slidably disposed within the lumen, with a distal portion of the elongate member configured to move between a first configuration when disposed within the lumen, and a second configuration when disposed distally beyond the sharpened distal end. The distal portion of the elongate member may be substantially linear in the first configuration, and substantially non-linear in the second configuration. The second configuration may include a loop, spiral or figure-eight shape. The distal portion may be split along a longitudinal axis of the elongate member to define first and second splines. The first and second splines may be substantially co-linear with the elongate member in the first configuration. The first and second splines may form Y-shape, T-shape or W-shape in the second configuration. Alternatively, the first and second splines form substantially spherical or oblong structures in the second configuration.

In another aspect, the present disclosure relates to a system comprising a needle that includes a proximal end, a sharpened distal end, and a lumen extending therebetween. An elongate member may be slidably disposed within the lumen. The elongate member may include a control rod, and a sheath slidably disposed around the control rod, with a distal portion of the elongate member configured to move between a first configuration when disposed within the lumen, and a second configuration when disposed distally beyond the sharpened distal end. A distal portion of the sheath may include at least one slit formed therein, wherein a distal end of the control rod is attached to a distal end of the sheath. The distal portion of the sheath may move from the second configuration to the first configuration by distally advancing the sheath over the control rod. Alternatively, the distal portion of the sheath may move from the first configuration to the second configuration by proximally retracting the control rod through the sheath. Alternatively, the distal portion of the sheath may move from the first configuration to the second configuration by distally advancing the sheath over the control rod. The distal portion of the sheath may move from the second configuration to the first configuration by distally advancing the control rod through the sheath. Alternatively, the distal portion of the sheath may move from the second configuration to the first configuration by distally retracting the sheath over the control rod. The distal portion of the sheath may form a basket in the second configuration.

In another aspect, the present disclosure relates to a method comprising advancing a penetrating a needle with a sharpened distal end and lumen running from a proximal end to the distal end through a tissue wall of a first body lumen and a tissue wall of a second body lumen adjacent to the first body lumen, and distally advancing an elongate member through the lumen of the needle such that the distal portion of the elongate member moves to a second configuration in contact with a portion of the tissue wall of the second body lumen to effect the position of the second body lumen relative to the first body lumen. The method may further include withdrawing the needle from over the elongate member and advancing a stent delivery system over the elongate member such that a distal end of the stent delivery system forms opposing holes in the tissue walls of the first and second body lumens. The method may further include deploying a stent from the stent delivery systems between the first and second body lumens. The method may further include distally retracting the elongate member through the stent delivery system and removing the stent delivery system.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. In the figures.

DETAILED DESCRIPTION

The present disclosure is not limited to the particular embodiments described. The terminology used herein is for the purpose of describing particular embodiments only, and is not intended to be limiting beyond the scope of the appended claims. Unless otherwise defined, all technical terms used herein have the same meaning as commonly understood by one of ordinary skill in the art to which the disclosure belongs.

Although embodiments of the present disclosure are described with specific reference to certain procedures, such as a gastrojejunostomy procedure, the systems and methods described herein may be used to position a fluid conduit between a variety of adjacent tissue walls, organs, vessels and/or body lumens.

As used herein, the singular forms "a," "an," and "the" are intended to include the plural forms as well, unless the context clearly indicates otherwise. It will be further understood that the terms "comprises" and/or "comprising," or "includes" and/or "including" when used herein, specify the presence of stated features, regions, steps elements and/or components, but do not preclude the presence or addition of one or more other features, regions, integers, steps, operations, elements, components and/or groups thereof.

As used herein, the term "distal" refers to the end farthest away from the medical professional when introducing a device into a patient, while the term "proximal" refers to the end closest to the medical professional when introducing a device into a patient.

In various of the embodiments described here and in other embodiments, the present disclosure relates to a system which prevents or minimizes movement between tissue walls during a transmural medical procedure in which a direct visual image and/or control of the distal tissue wall is difficult or not available.

Figure 1A:
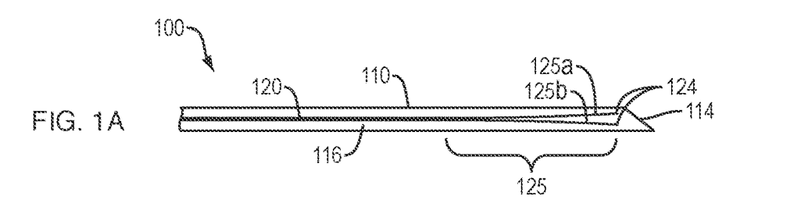
FIGS. 1A-1G provide perspective views of a system in a delivery (FIG. 1A) and deployed (FIGS. 1B-1G) configurations, according to embodiments of the present disclosure.

Referring to FIG. 1A, in one embodiment, a system 100 of the present disclosure may include a tissue-penetrating element 110 (e.g., needle, etc.) comprising a proximal end (not shown), a sharpened distal end 114 and a lumen 116 extending therebetween. An elongate member 120 (e.g., rail, guidewire, etc.) comprising a proximal end (not shown) and a distal end 124 may be slidably disposed within the lumen 116 of the tissue-penetrating element 110. A distal portion 125 of the elongate member 120 may be split (e.g., divided) along a longitudinal axis thereof to define first and second splines 125a, 125b (e.g., tines, forks, branches, prongs, arms, etc.). The first and second splines 125a, 125b may be substantially co-linear with a longitudinal axis of the elongate member 120 when disposed within the lumen 116 of the tissue penetrating element 110. At least the distal portion 125 of the elongate member 120 may include a variety of shape memory materials as are known in the art (e.g., metals, alloys, polymers, and the like), configured to move between a first configuration when disposed within lumen 116 of the tissue-penetrating element 110, and a second configuration when disposed distally beyond the sharpened distal end 114 of the tissue-penetrating element 110. The distal portion 125 of the elongate member 120 is not limited to two splines, but may include any number of splines (e.g., three or more splines).

Figure 1B:
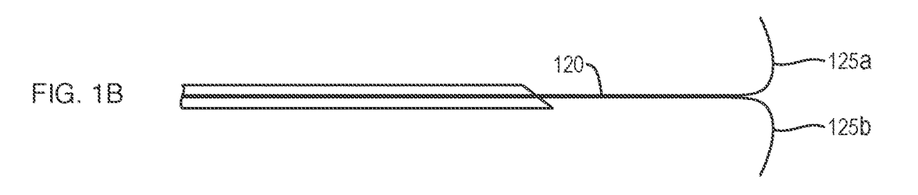
Figure 1C:
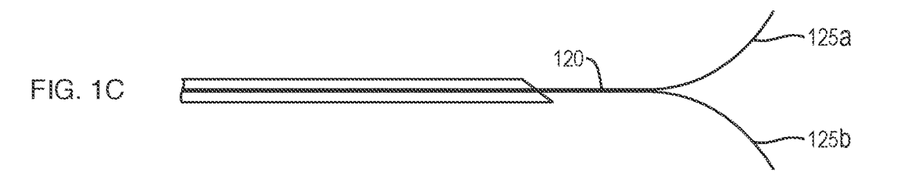
Figure 1D:
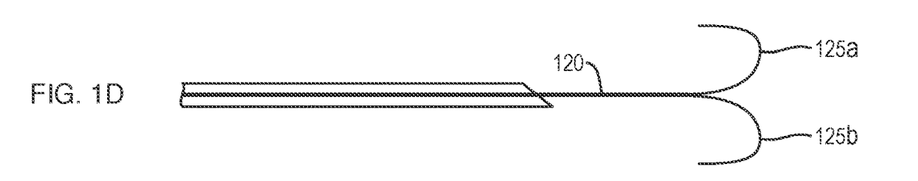
Figure 1E:
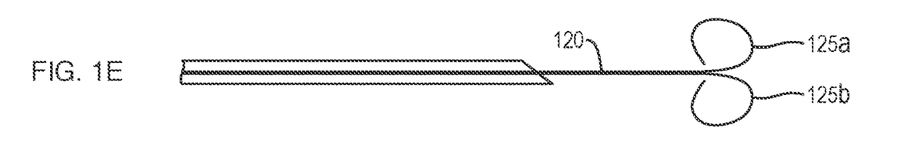
Figure 1F:
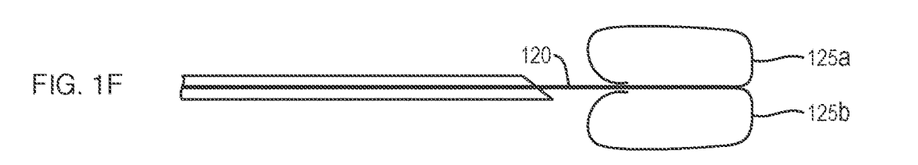
Figure 1G:
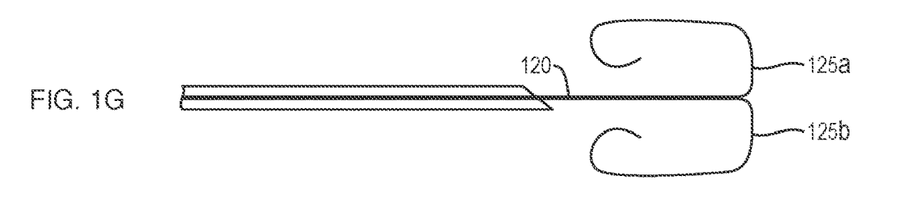

Referring to FIG. 1B, in one embodiment, the first and second splines 125a, 125b may move or deflect substantially perpendicular to the longitudinal axis of the elongate member 120 to form a "T-shape" when in the second configuration. Referring to FIG. 1C, in one embodiment, the first and second splines 125a, 125b may move or deflect substantially tangential to the longitudinal axis of the elongate member 120 to form a "Y-shape" when in the second configuration. Referring to FIG. 1D, in one embodiment, the first and second splines 125a, 125b may bend back along/ over and parallel to the longitudinal axis of the elongate member 120 to form a "W-shape" when in the second configuration. Referring to FIG. 1E, in one embodiment, the first and second splines 125a, 125b may curl back along/ over the longitudinal axis of the elongate member 120 to form opposed substantially spherical (e.g., circular) shapes when in the second configuration. Referring to FIG. 1F, in one embodiment, the first and second splines 125a, 125b may curl back along/over the longitudinal axis of the elongate member 120 to form opposed substantially oblong (e.g., elliptical, elongate sphere, etc.) shapes when in the second configuration. Referring to FIG. 1G, in one embodiment, the first and second splines 125a, 125b may curl back along/ over the longitudinal axis of the elongate member to form opposed substantially oblong shapes, which are spaced apart (e.g., separated) from the longitudinal axis of the elongate member when in the second configuration. Although the distal portions 125 of the elongate members 120 are depicted as forming substantially symmetrical structures, in various embodiments the first and second splines 125a, 125b may form any combination of the second configurations depicted in FIGS. 1B-1G, or other configurations not depicted. In various embodiments, when in the second configuration, the first and second splines 125a, 125b may move (e.g., deflect, bend, twist, compress, etc.) independent of each other when placed in contact with an inner surface of a tissue wall, as discussed below.

Figure 2A:
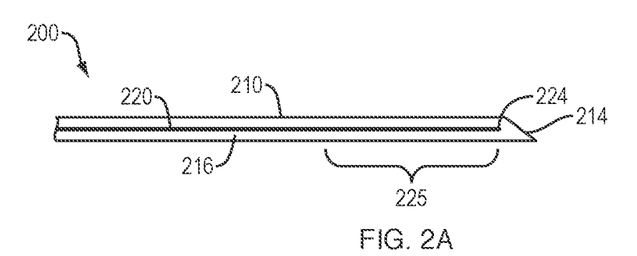
FIGS. 2A-2E provide perspective views of a system in a delivery (FIG. 2A) and deployed (FIGS. 2B-2E) configurations, according to embodiments of the present disclosure.
Figure 2B:
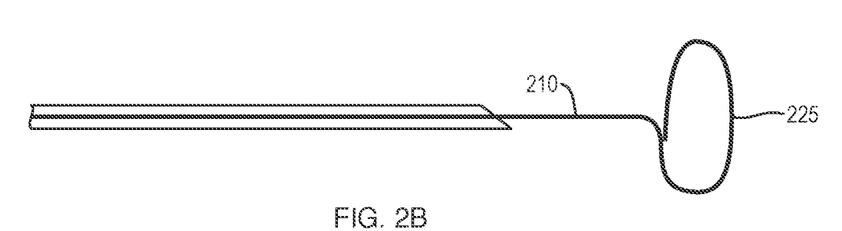
Figure 2C:
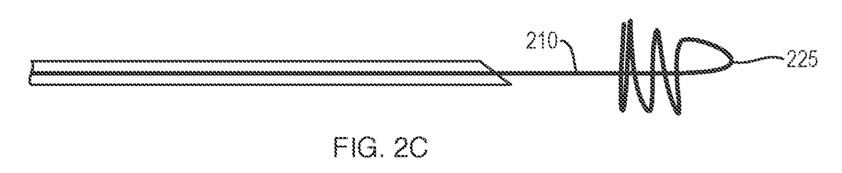
Figure 2D:
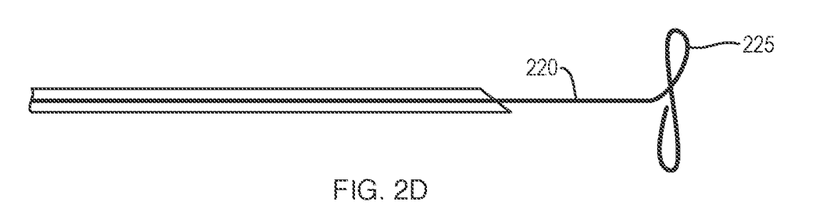
Figure 2E:
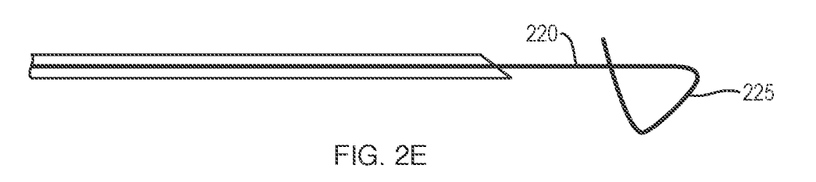

Referring to FIG. 2A, in one embodiment, a system 200 of the present disclosure may include a tissue-penetrating element 210 (e.g., needle, etc.) comprising a proximal end (not shown), a sharpened distal end 214 and a lumen 216 extending therebetween. An elongate member 220 (e.g., rail, guidewire, etc.) comprising a proximal end (not shown) and a distal end 224 may be slidably disposed within the lumen 216 of the tissue-penetrating element 210. At least the distal portion 225 of the elongate member 220 may include a variety of shape memory materials as are known in the art (e.g., metals, alloys, polymers, and the like), configured to move between a first configuration when disposed within lumen 216 of the tissue-penetrating element 210, and a second configuration when disposed (advanced) distally beyond the sharpened distal end 214 of the tissue-penetrating element 210. Referring to FIG. 2B, in one embodiment, the distal portion 225 of the elongate member 220 may form a "loop" or "hoop" when in the second configuration. Referring to FIG. 2C, in one embodiment, the distal portion 225 of the elongate member 220 may bend approximately 180 degrees relative to the longitudinal axis of the elongate member 220 to form a "reverse coil" or "reverse spiral"

around a portion of the elongate member 220 when in the second configuration. Referring to FIG. 2D, in one embodiment, the distal portion 225 of the elongate member 220 may form a "figure-eight," "lasso," or "cork screw" shape when in the second configuration. Referring to FIG. 2E, in one embodiment, the distal portion 225 of the elongate member 220 may bend to form a "cross-bar" that extends across the longitudinal axis of the elongate member 220 when in the second configuration.

The various second configurations of the distal portions 125, 225 may provide a number of additional benefits to further secure/immobilize the distal tissue wall when the elongate member 120, 220 is proximally retracted. By way of non-limiting example, the ends of the first and second prongs 125a, 125b depicted in any of FIGS. 1B-1D may partially penetrate/embed within the distal tissue wall. A portion of the splines 125a, 125b in any of FIGS. 1B-1G, or the distal portion 225 of the elongate member 220 of FIGS. 2B-2E, may include one or more hooks, barbs, prongs, etc. to provide enhanced friction against an inner wall of the distal tissue. In various embodiments, the splines 125a, 125b and/or distal portion 225 of the elongate member 220 may provide a gradual increase in retention pressure when the elongate member 120, 220 is proximally retracted, thereby allowing the medical professional to exert more or less immobilizing force against the inner surface of the distal tissue wall as necessary throughout the course of the medical procedure. In addition, or alternatively, a portion of the surface of the splines 125a, 125b of any of FIGS. 1B-1D may include a sharpened edge configured to enlarge or expand the puncture hole created by the sharpened distal end 114 of the tissue-penetrating element 110 within the first and/or second tissue walls. One, or both, of the spherical or oblong shapes of FIGS. 1E-1G, respectively, may deflect (e.g., bend, splay, etc.) away from the longitudinal axis of the elongate member 120 to provide retention pressure across a larger surface area of the distal tissue.

Figure 3A:
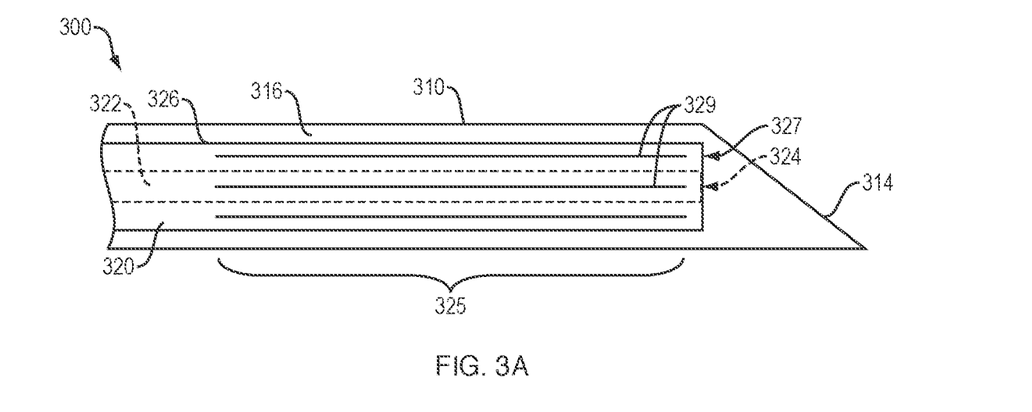
FIGS. 3A-3C provide perspective views of a system in a delivery (FIGS. 3A-3B) and deployed (FIG. 3C) configuration, according to one embodiment of the present disclosure.
Figure 3B:
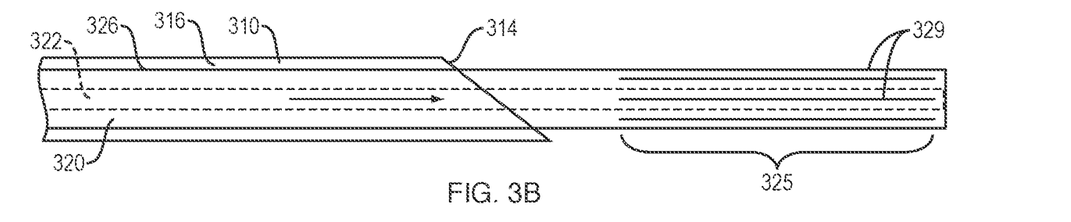
Figure 3C:
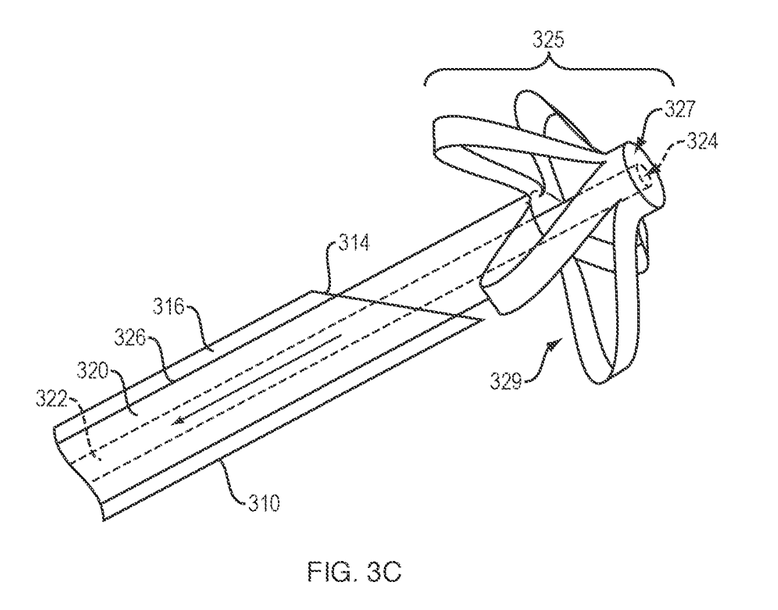

Referring to FIGS. 3A-3C, in one embodiment, a system 300 of the present disclosure may include a tissue-penetrating element 310 (e.g., needle, etc.) comprising a proximal end (not shown), a sharpened distal end 314 and a lumen 316 extending therebetween. An elongate member 320 may be slidably disposed within the lumen 316 of the tissue-penetrating element 310. The elongate member 320 may include a control rod 322 slidably disposed within a sheath 326. A distal end 324 of the control rod 322 may be attached to a distal end 327 of the sheath 326. A distal portion 325 of the sheath 326 may include one or more slits 329 formed therein, and be configured to move between a first configuration when disposed within lumen 316 of the tissue-penetrating element 310 (FIG. 3A), and a second configuration when disposed distally beyond the sharpened distal end 314 of the tissue-penetrating element 310 (FIG. 3C).

For example, at least the distal portion 325 of the sheath 326 may include a variety of materials, including, but not limited to shape memory materials, e.g., nitinol, polyether ether ketone (PEEK), etc., into which the one or more slits 329 are formed using, e.g., laser cutting. The elongate member 320 may be advanced through the lumen 316 of the tissue-penetrating element 320 by distally advancing the control rod 322 (FIG. 3B). In one embodiment, the distal portion 325 of the sheath 326 may move to the second configuration by distally advancing the sheath 326 over/along the control rod 322. Alternatively, the distal portion 325 of the sheath 326 may move to the second configuration by proximally retracting the control rod 322 through/within the sheath 326 (FIG. 3C). In either embodiment, the one or more slits 329 may allow the distal portion 325 to form a "basket" that includes a series of arms or petals configured to engage the distal tissue wall. In one embodiment, the distal portion 325 may include one or more hooks, barbs, prongs, etc. for enhanced friction against the distal tissue wall. Although FIGS. 3A-3C depict an embodiment in which the distal portion 325 includes 5 slits configured to form 5 arms or petals when in the second configuration, in various embodiments, the distal portion may include any number of slits configured to form a variety of second configurations.

In one embodiment, the elongate members 120, 220, 320 disclosed herein may be disposed within, and delivered through, a tissue-penetrating element 110, 210, 310 that includes a 19 or 21-gauge needle used for fine-needle aspiration (FNA) or fine-needle biopsy (FNB) procedures, as are known in the art. In addition, or alternatively, the tissue penetrating elements 110, 210, 310 and/or elongate members 120, 220, 320 may beneficially include a coating, such as a fluorinated polymer or paralene, to provide electrical insulation and/or improved lubricity. To prevent coring of the proximal or distal tissue walls, the distal portion 125, 225, 325 of the elongate member 120, 220, 320 may be configured to obturate the lumen 116, 216, 316 at or near the sharpened distal end 114, 214, 314 of the tissue-penetrating element 110, 210, 310.

Figure 4A:
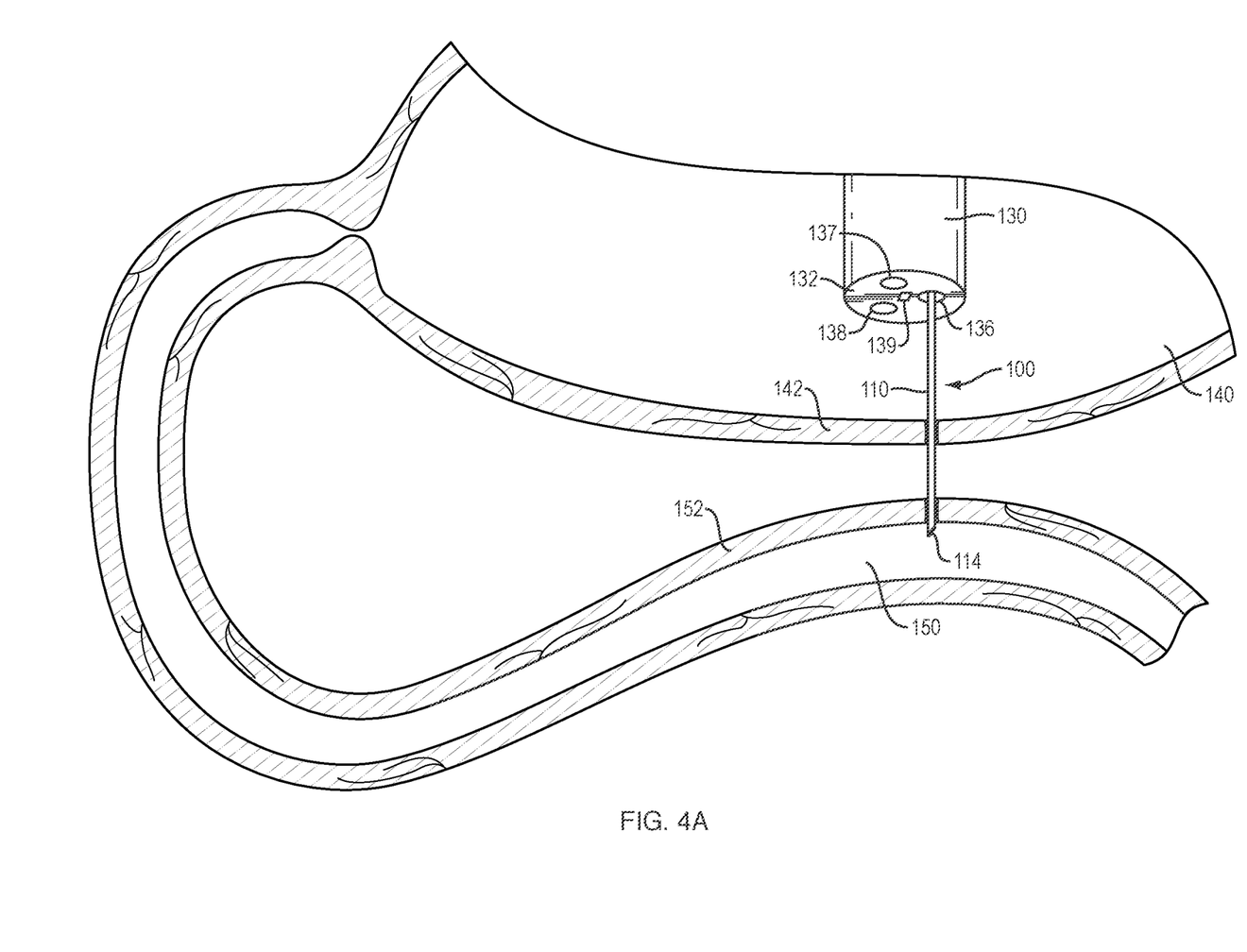
FIGS. 4A-4F provide perspective views of a stent deployment procedure using a system, according to one embodiment of the present disclosure.

In one embodiment, a system 100, 200, 300 of the present disclosure may be delivered through the working channel of an endoscope. Referring to FIG. 4A, in use and by way of example, an ultrasound endoscope 130 may be advanced through the esophagus into a first body lumen 140 (e.g., the stomach). The distal end 132 of the endoscope 130 may include a camera 137, light source 138 and ultrasound transducer 139. Using the direct view (e.g., the light source 138 and camera 137) the distal end 132 of the endoscope 130 may be positioned adjacent to a tissue wall 142 (e.g., proximal tissue wall) of the first body lumen 140 which is in the vicinity of the tissue wall 152 (e.g., distal tissue wall) of a second body lumen 150 (e.g., the duodenum or jejunum). The second body lumen 150 may then be imaged through the first tissue wall 142 by switching the endoscope 130 from the direct view to an ultrasound view (e.g., turning off the light source 138 and turning on the ultrasound transducer 139). The system 100 may then be advanced through the working channel 136 of the endoscope 130 such that the sharpened distal end 114 of the tissue-penetrating element 110 penetrates the first and second tissue walls 142, 152, and extends into the second body lumen 150.

Figure 4B:
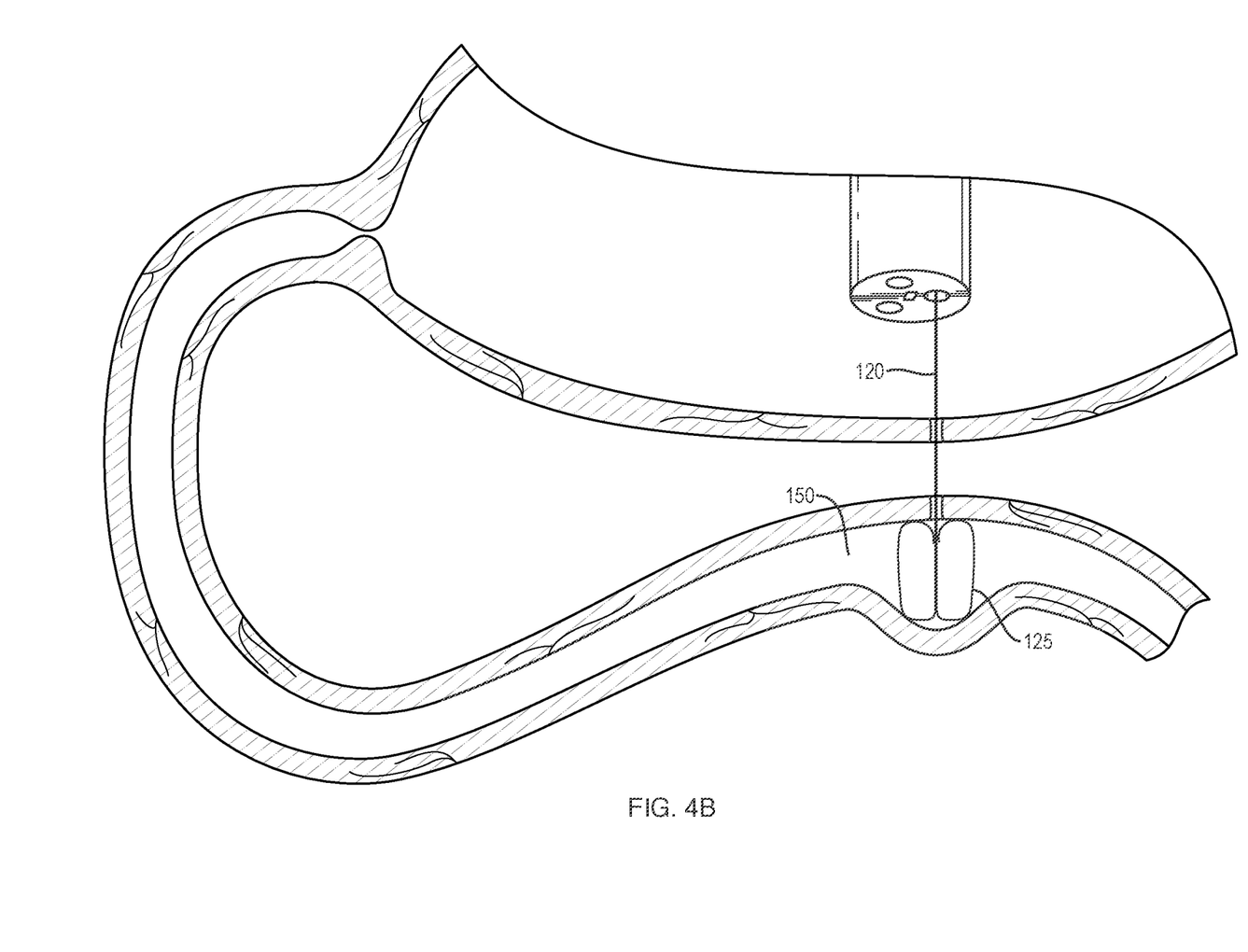

Referring to FIG. 4B, the elongate member 120 may be distally advanced beyond the sharpened distal end of the tissue-penetrating element such that the distal portion 125 moves to the second configuration within the second body lumen 150. The tissue-penetrating element may then be removed along/over the elongate member 120 (e.g., proximally withdrawn) through the working channel 136 of the endoscope 130. The elongate member 120 may then be proximally retracted to place the distal portion 125 in contact with an inner portion of the second distal tissue wall 152, and with sufficient force to minimize or prevent (e.g., anchor) movement of the distal tissue wall 162 relative to the proximal tissue wall 152.

Figure 4C:
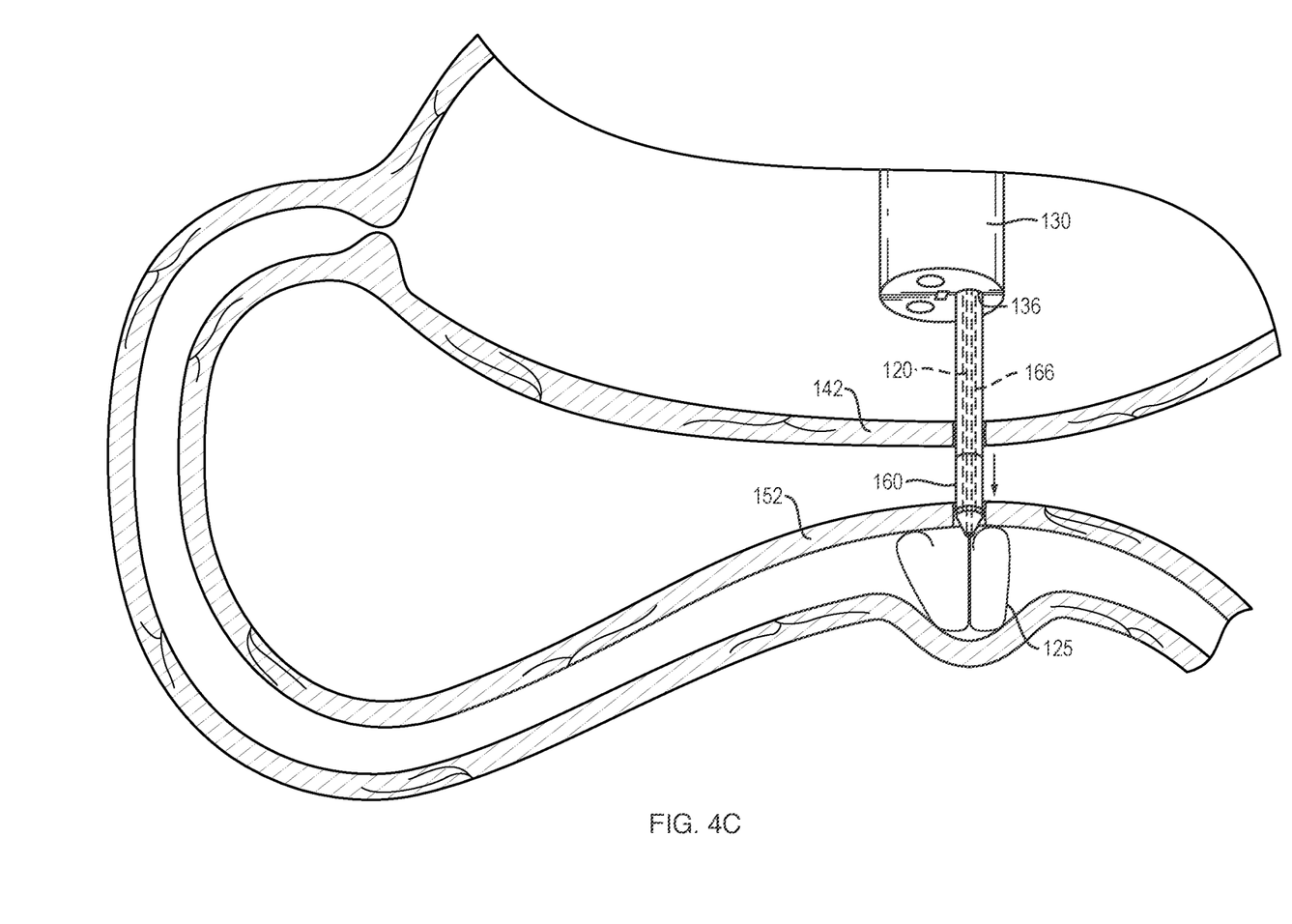

Referring to FIG. 4C, with the proximal and distal tissue walls 142, 152 sufficiently immobilized with respect to each other, a stent delivery system 160 with a stent 162 loaded thereon may be advanced through the working channel 136 of the endoscope 130. The stent delivery system 160 may include a lumen 166 configured to slide over/along the elongate member 120. The distal end of the stent delivery system 160 may include a cutting element, e.g., electrocautery surface, configured to create opposed openings (e.g., holes) through the first and second tissue walls 142, 152. In one embodiment, the distal portion 125 of the elongate member 120 may provide a firm/secure platform against which the electrocautery surface of the stent delivery system 160 may press when forming the opposed openings. The distal portion 125 may provide the additional benefit of establishing separation between the opposite tissue wall of the second body lumen 150 and the stent delivery system to prevent unintentional cutting by the cutting element. In one embodiment, one (or both) of the oblong portions of the distal portion 125 may deflect away from the longitudinal axis of the elongate member 120 to provide retention pressure across a larger surface area of the distal tissue wall. In addition, or alternatively, the ability of the distal portion (s) 125 to deflect away from the longitudinal axis of the elongate member 120 may provide a space to allow: 1) the cutting element of the delivery system 160 to fully penetrate the second body lumen 150, 2) unhindered deployment of the distal flange 166 of stent 162 (FIG. 4D), and/or 3) introduction of an additional cutting element to further dilate (e.g., enlarge) the tissue opening without imparting excessive force on the opposite tissue wall of the second body lumen 150. In addition, the oblong shape may provide a degree of flexibility to the distal portion 125, such that the stent delivery system 160 may be advanced a sufficient distance into the second body lumen 150 to deploy the distal flange without further pushing the distal portion 125 against the opposite tissue wall. The distal portion 125 of the elongate member 120 may include a soft and/or compliant surface or coating to prevent trauma to the opposite tissue wall in the event contact therebetween occurs.

Figure 4D:
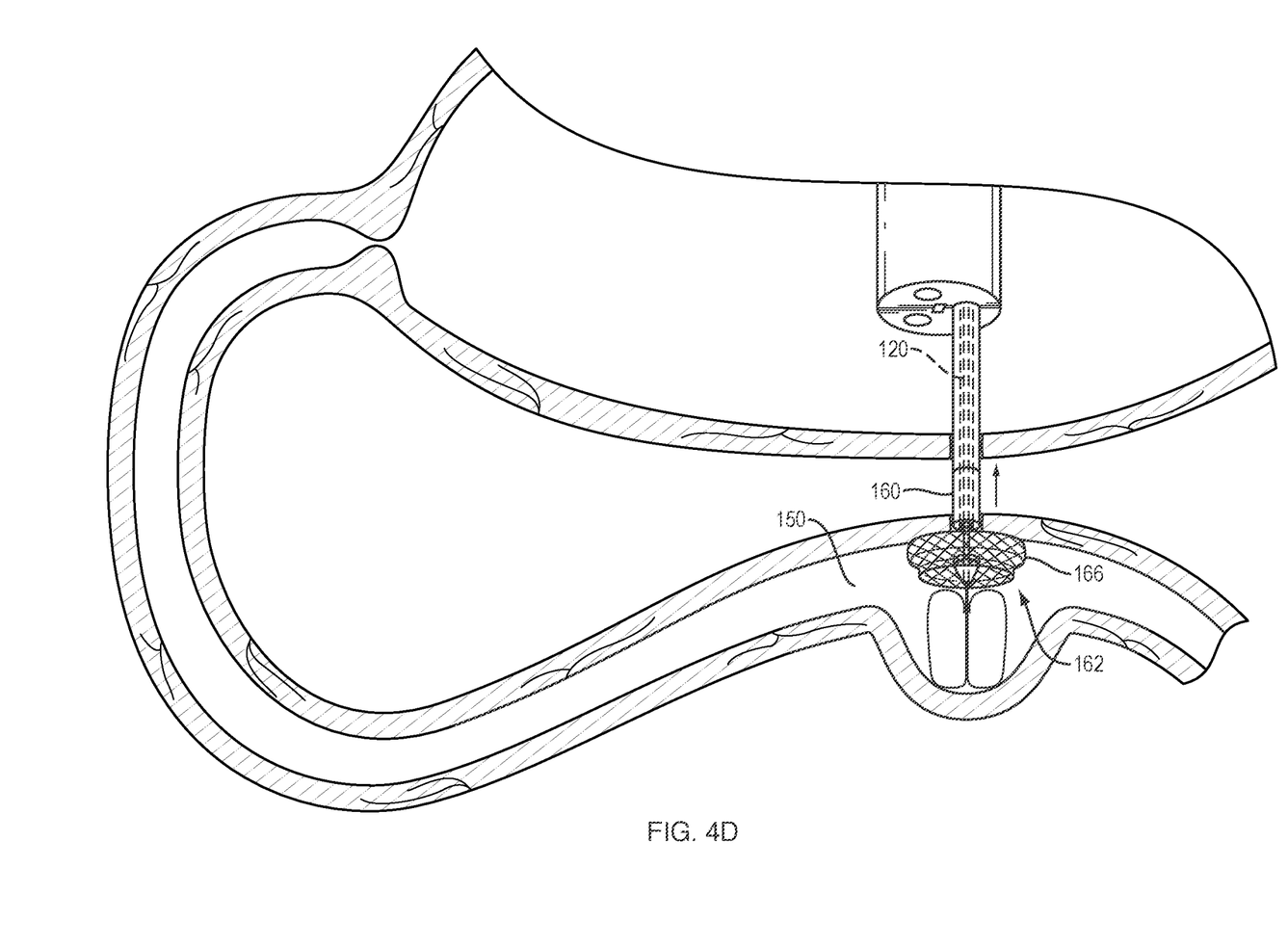
Figure 4E:
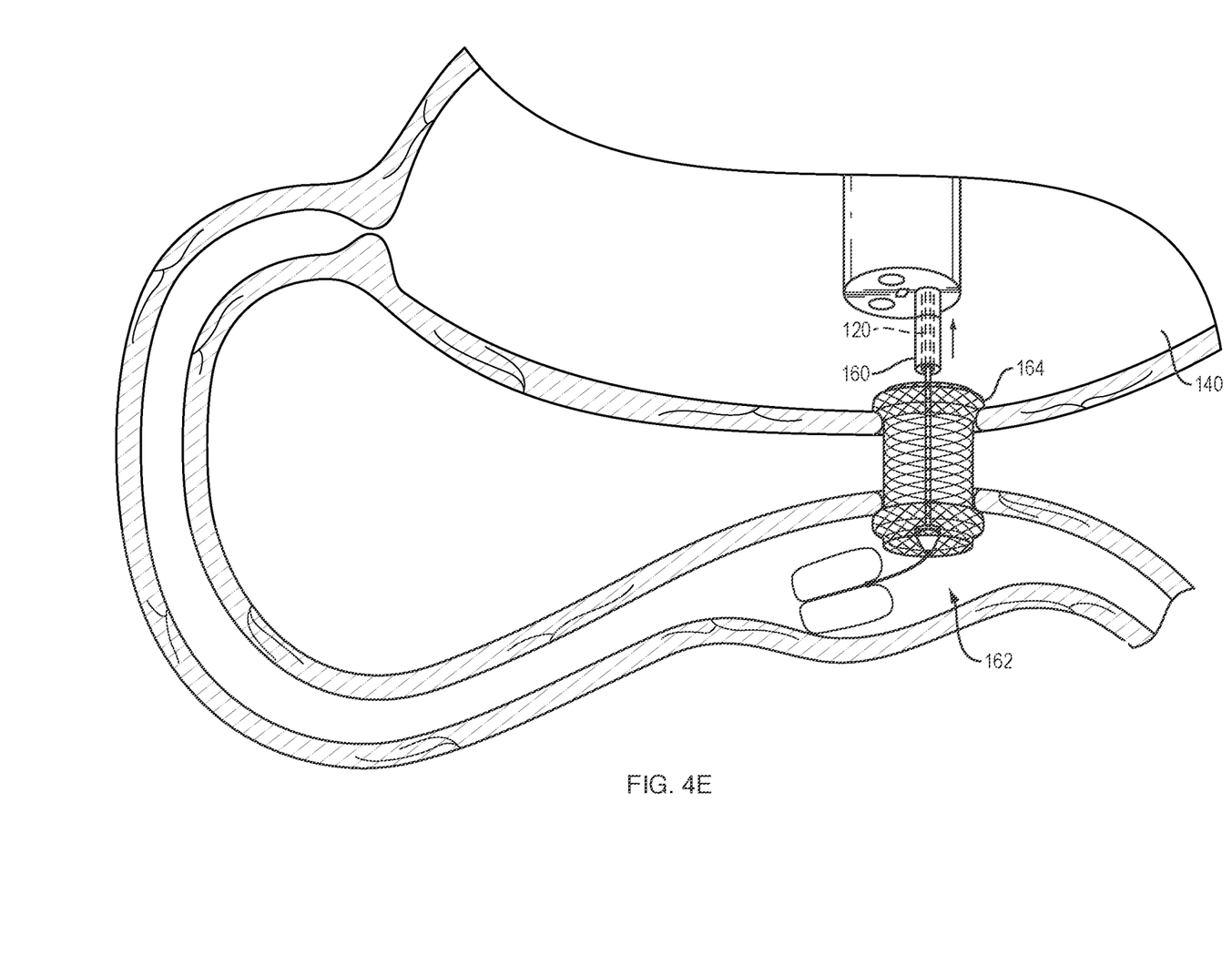
Figure 4F:
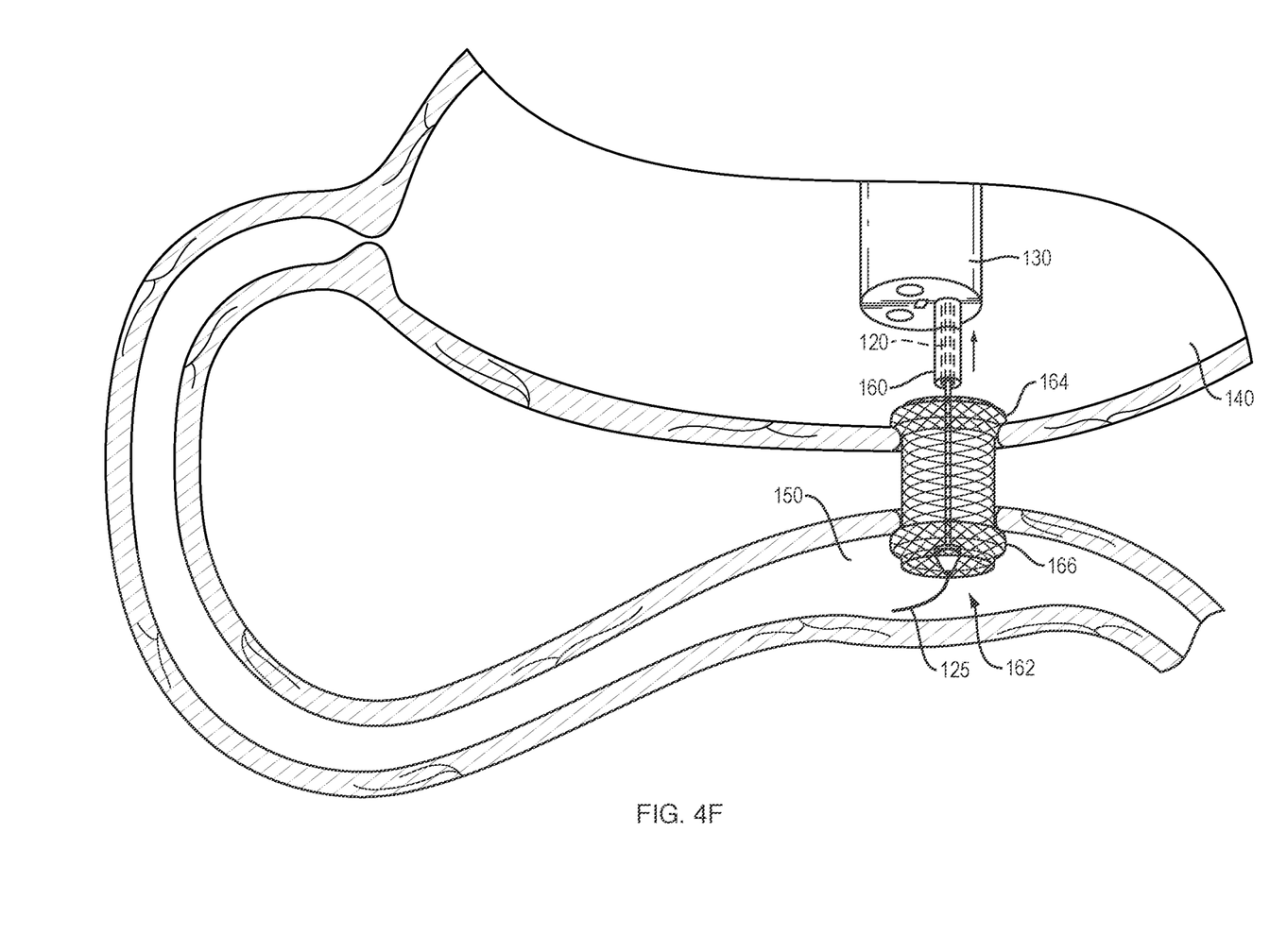

Referring to FIG. 4D, an outer portion of the stent delivery system 160 may then be proximally retracted over the inner lumen 166, elongate member 120 and stent 162 to deploy the distal flange 165 of a stent 162 within the second body lumen 150. Referring to FIG. 4E, the outer portion of the stent delivery system 160 may be further retracted over the inner lumen 166, the elongate member 120 and the stent 162 to deploy the proximal flange 164 of the stent 162 within the first body lumen 140. Referring to FIG. 4F, with the proximal and distal flanges 164, 165 properly deployed within the first and second body lumens 140, 150, the elongate member 120 may be proximally retracted with sufficient force such that the distal portion 125 moves from the second configuration to the first configuration for removal through the lumen 166 of the stent delivery system. The endoscope 130, stent delivery system 160 and elongate member 120 may then be removed from the patient. The stent configuration depicted in FIGS. 4D-4F is provided by way of non-limiting example, and may include a variety of different shapes, configurations, orientations, dimensions and/or materials as required to provide a flow pathway between adjacent tissue walls. In addition, an outer and/or inner surface of the stent may be fully or partially covered (e.g., across the saddle region between the proximal and distal flanges) to prevent fluid leakage between the tissue walls. Although FIGS. 4E-4F depict a gap between the tissue walls of the first and second body lumens 140, 150 after placement of the stent, in other embodiments the procedure may result in the tissue walls being apposed into contact with each other along the saddle region, with the proximal and distal flanges providing contact with the respective inner surface of each tissue wall.

Although the systems 100, 200, 300 disclosed herein are configured to minimize or prevent proximal and distal tissue walls from moving away from each other during a medical procedure, rather than moving either tissue wall towards the other, in one embodiment, the elongate member 120, 220, 320 may be proximally retracted with sufficient force such that the distal portion 125, 225, 325 pulls the distal tissue wall over the stent delivery system 160 for deployment of the distal flange within the second body lumen 150.

Figure 5A:
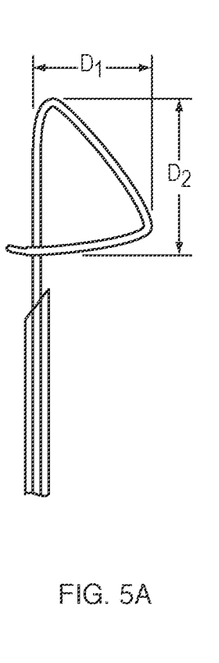
FIGS. 5A-5C provide perspective views of a stent deployment using the system of FIG. 2E, according to one embodiment of the present disclosure.
Figure 5B:
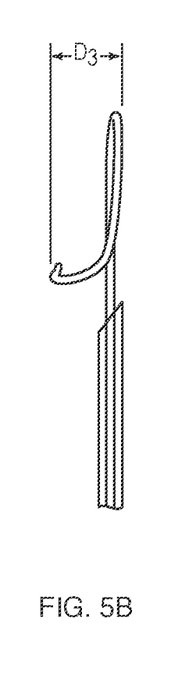
Figure 5C:
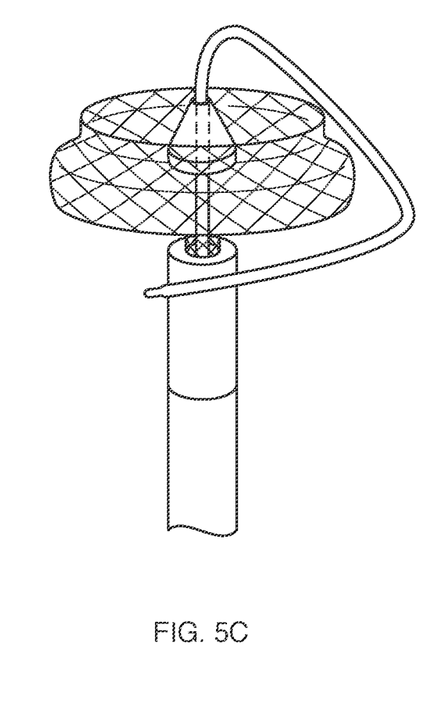

Referring to FIGS. 5A-5C, in one embodiment, the distal portion 225 of the elongate member 220 of FIG. 2E may include a first dimension $D_1$ (e.g., a width), a second dimension $D_2$ (e.g., a height) and a third dimension $D_3$ (e.g., an elevation) relative to the longitudinal axis of the elongate member 220. By way of non-limiting example, the first dimension $D_1$ may be approximately 1.00 inches, the second dimension $D_2$ may be approximately 0.78 inches and the third dimension $D_3$ may be approximately 0.33 inches. In various embodiments, the first, second and third dimensions $D_1$-$D_3$ of the distal portion 225 may provide a space within which the distal flange 165 of a stent 162 may be deployed (e.g., within a second body lumen, as outlined above), while the distal portion 225 of the elongate member maintains contact with the tissue wall of the second body lumen throughout the stent deployment procedure.

In various embodiments, the elongate members 120, 220, 320 disclosed herein may be include sufficient flexibility and strength to repeatedly slide into and out of a tissue-penetrating element, or other medical device (e.g., retraction catheter, etc.), without breaking/fracturing and while maintaining the ability to move to the second configuration within the second body lumen (e.g., to provide the requisite retention strength). In addition, any of the elongate members 120, 220, 320 disclosed herein may include a suitable coating to facilitate slidable motion within a tissue-penetrating element, or other medical device. In various embodiments, such coating(s) may also impart dielectric strength the all, or a portion of, the elongate member.

The medical devices of the present disclosure are not limited to endoscopes, and may include a variety of medical devices for accessing body passageways, including, for example, catheters, bronchoscopes, ureteroscopes, duodenoscopes, colonoscopes, arthroscopes, cystoscopes, hysteroscopes, and the like. Finally, although the embodiments of the present disclosure have been described in use with an endoscope, the systems of the present disclosure may be positioned within the patient in the absence of an accompanying medical device.

All of the devices and/or methods disclosed and claimed herein can be made and executed without undue experimentation in light of the present disclosure. While the devices and methods of this disclosure have been described in terms of preferred embodiments, it may be apparent to those of skill in the art that variations can be applied to the devices and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

What is claimed is:
1. A system, comprising:
 a needle, comprising:
  a proximal end;
  a sharpened distal end; and
  a lumen extending therebetween; and an elongate member slidably disposed within the needle lumen and having a proximal end and a distal end, wherein a distal portion of the elongate member is configured to move between a first configuration when disposed within the needle lumen, and a second configuration when disposed distally beyond the sharpened distal end of the needle;

wherein when in the second configuration and in contact with a tissue wall of a distal body lumen, the distal portion of the elongate member is configured to minimize movement of the tissue wall of the distal body lumen relative to a tissue wall of a proximal body lumen as the proximal end of the elongate member is moved proximally.

2. The system of claim 1, wherein the distal portion of the elongate member is substantially linear in the first configuration.

3. The system of claim 1, wherein the distal portion of the elongate member is substantially non-linear in the second configuration.

4. The system of claim 1, wherein the second configuration is selected from the group consisting of a loop, spiral, and figure-eight shape.

5. The system of claim 1, wherein the distal portion is split along a longitudinal axis of the elongate member to define first and second splines.

6. The system of claim 5, wherein the first and second splines are substantially co-linear with the elongate member in the first configuration.

7. The system of claim 5, wherein the first and second splines form a Y-shape in the second configuration.

8. The system of claim 5, wherein the first and second splines form a T-shape in the second configuration.

9. The system of claim 5, wherein the first and second splines form a W-shape in the second configuration.

10. The system of claim 5, wherein the first and second splines form substantially spherical structures in the second configuration.

11. The system of claim 5, wherein the first and second splines form substantially oblong structures in the second configuration.

12. The system of claim 1, wherein in the second configuration the distal portion of the elongate member provides a gradual increase in retention pressure on the tissue wall of the distal body lumen as the elongate member is proximally retracted.

13. The system of claim 1, wherein in the second configuration the distal portion of the elongate member maintains a space between opposite tissue walls of the distal body lumen.

14. A system, comprising:
a needle, comprising:
a proximal end;
a sharpened distal end; and
a lumen extending therebetween; and
an elongate member slidably disposed within the lumen, wherein a distal portion of the elongate member is configured to move between a first configuration when disposed within the needle lumen, and a second configuration different in shape than the first configuration when disposed distally beyond the sharpened distal end of the needle; and
a stent configured to be advanced over the elongate member and to the distal portion of the elongate member in the second configuration.

15. The system of claim 14, wherein the elongate member comprises a control rod and a sheath slidably disposed around the control rod, wherein a distal portion of the sheath is movable between the first configuration and the second configuration by advancing or retracting the control rod relative to the sheath.

16. A method, comprising:
advancing a penetrating needle with a sharpened distal end and lumen running from a proximal end of the needle to the distal end of the needle through a first tissue wall of a first body lumen and a second tissue wall of a second body lumen positioned spaced apart from the first body lumen; and
distally advancing an elongate member through the lumen of the needle such that a distal portion of the elongate member moves to a second configuration in contact with a portion of the second tissue wall of the second body lumen to affect the position of the second body lumen relative to the first body lumen.

17. The method of claim 16, further comprising withdrawing the needle from over the elongate member and advancing a stent delivery system over the elongate member such that a distal end of the stent delivery system forms opposing holes sufficient to accommodate the stent delivery system in the first and second tissue walls of the respective first and second body lumens.

18. The method of claim 17, further comprising deploying a stent from the stent delivery system spanning the first and second body lumens.

19. The method of claim 18, further comprising distally retracting the elongate member through the stent delivery system.

20. The method of claim 19, further comprising moving the stent within a space provided by the elongate member in the second configuration.

* * * * *